(12) United States Patent
Sommer

(10) Patent No.: US 7,497,689 B2
(45) Date of Patent: Mar. 3, 2009

(54) ELECTRICALLY CONDUCTIVE CONNECTION FOR A MEDICAL GANTRY

(75) Inventor: Andres Sommer, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/527,820

(22) Filed: Sep. 27, 2006

(65) Prior Publication Data

US 2007/0093100 A1    Apr. 26, 2007

(30) Foreign Application Priority Data

Sep. 30, 2005    (DE) .................. 10 2005 047 050

(51) Int. Cl.
*H05G 1/60*    (2006.01)

(52) U.S. Cl. .......................... 439/24; 378/15

(58) Field of Classification Search ............ 439/23–26; 378/15, 194–197; 310/241; 250/492.3
See application file for complete search history.

(56) References Cited

U.S. PATENT DOCUMENTS

| 2,632,860 | A | * | 3/1953 | Agron ...................... 310/241 |
| 3,322,950 | A | * | 5/1967 | Bailey et al. ................ 378/65 |
| 4,798,540 | A | * | 1/1989 | Bernardi ..................... 439/22 |
| 4,912,735 | A | * | 3/1990 | Beer .......................... 378/15 |
| 5,134,639 | A | * | 7/1992 | Vekstein et al. .............. 378/15 |
| 5,224,138 | A | * | 6/1993 | Hirao et al. .................. 378/15 |
| 5,554,848 | A | * | 9/1996 | Hermony et al. ....... 250/363.05 |
| 6,674,836 | B2 | * | 1/2004 | Harada et al. .............. 378/107 |
| 7,105,983 | B2 | * | 9/2006 | Day et al. ............. 310/323.01 |
| 7,120,547 | B2 | * | 10/2006 | Herrmann et al. ............. 702/85 |
| 7,123,682 | B2 | * | 10/2006 | Kotian et al. ................. 378/21 |
| 2003/0058984 | A1 | | 3/2003 | Susami et al. |
| 2005/0161618 | A1 | * | 7/2005 | Pedroni ..................... 250/492.3 |
| 2007/0195924 | A1 | * | 8/2007 | Krumme .................... 378/15 |

FOREIGN PATENT DOCUMENTS

| DE | 19717796 A1 | 10/1998 |
| DE | 19957621 C2 | 11/2001 |
| DE | 10146210 A1 | 4/2003 |
| DE | 10356109 A1 | 7/2005 |
| WO | WO 2005/058164 A1 | 6/2005 |

* cited by examiner

*Primary Examiner*—Neil Abrams
(74) *Attorney, Agent, or Firm*—Brinks, Hofer, Gilson & Lione

(57) ABSTRACT

An electrically conductive connection is provided. The electrically conductive connection includes a gantry, rotatable about a pivot axis, and a stand. The connection comprising a wireless electrical contact, and at least one defined rotary position of the gantry. The connection including a slipring and brush or a slipring and non-contact transmission. A radiation therapy system and method for operating a gantry of a radiation therapy system is also provided.

17 Claims, 2 Drawing Sheets

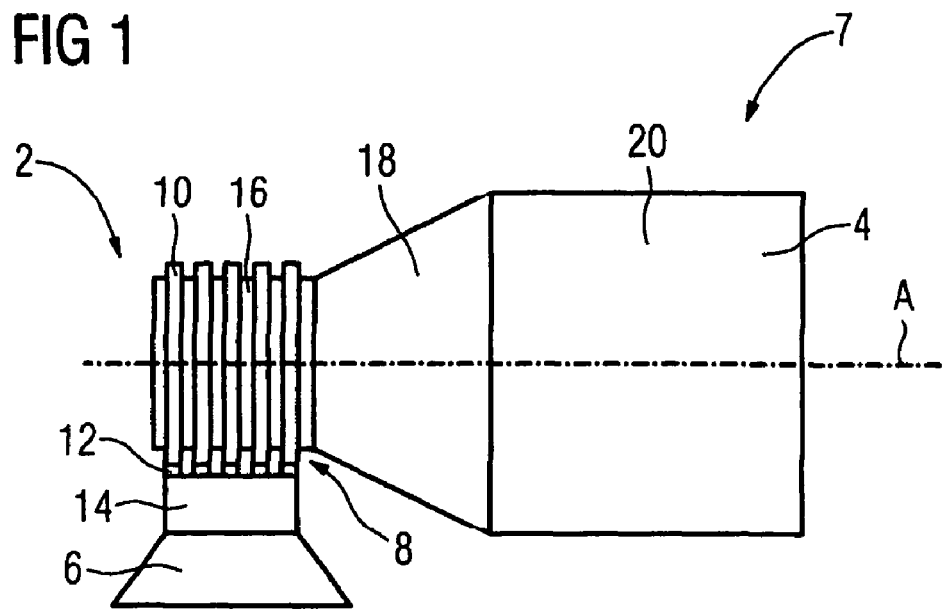
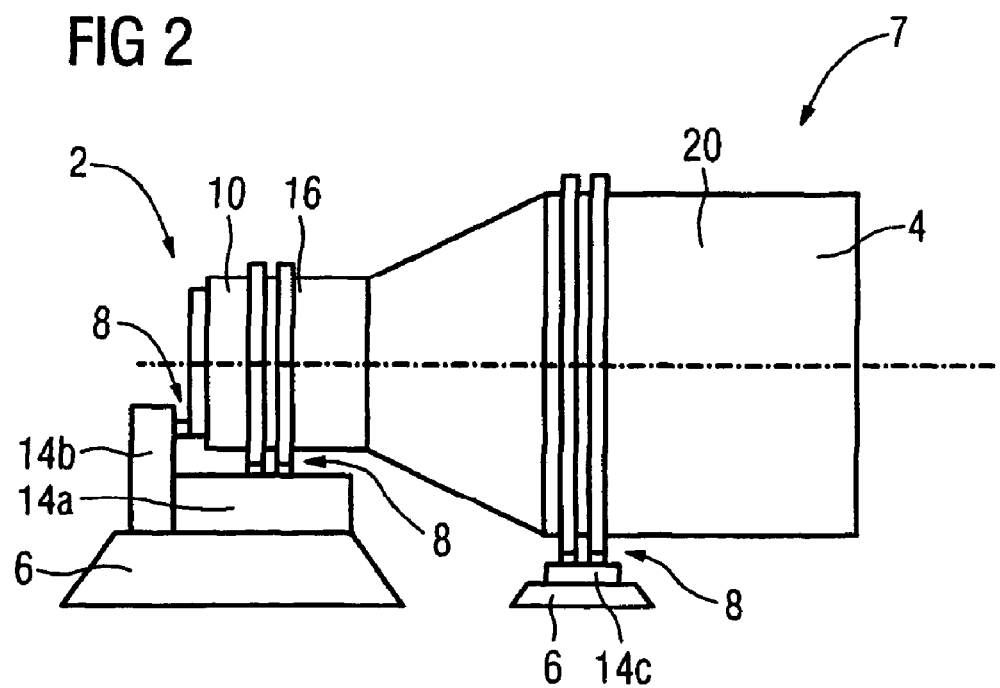

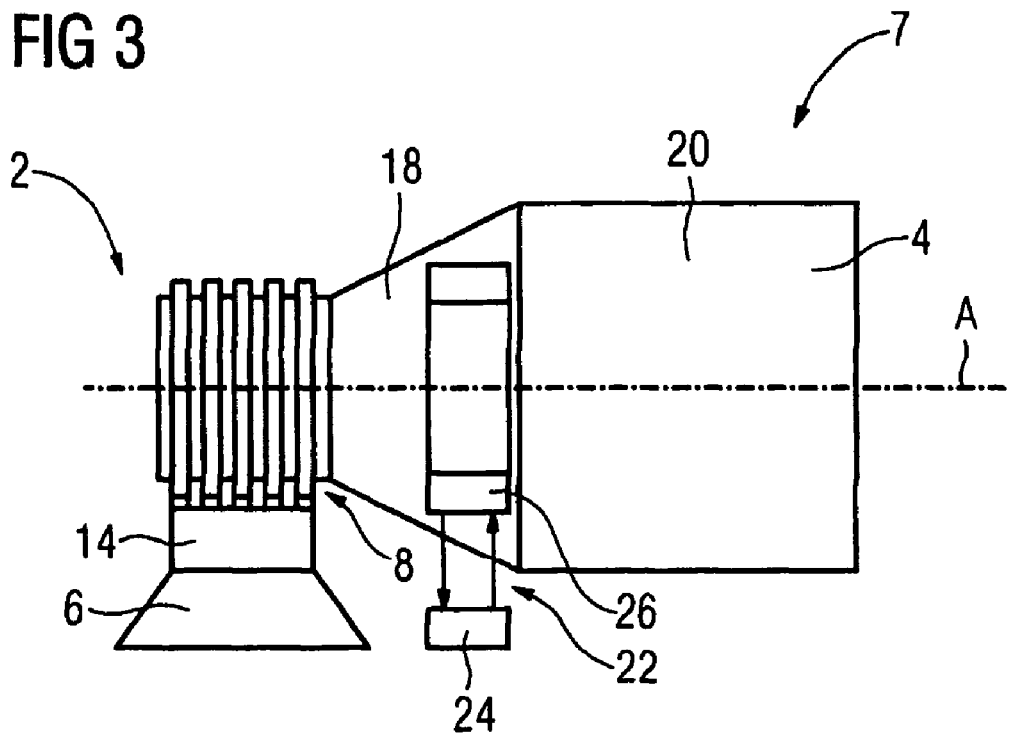
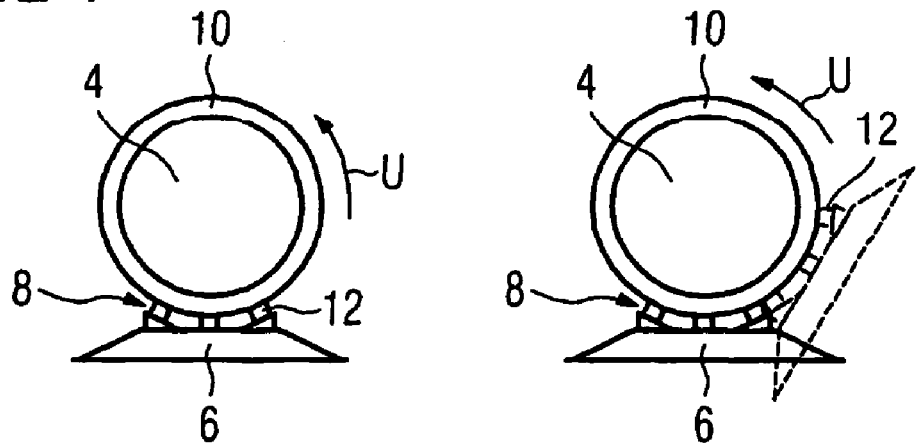

ELECTRICALLY CONDUCTIVE CONNECTION FOR A MEDICAL GANTRY

The present patent document claims the benefit of the filing date of DE 10 2005 047 050.5, filed Sep. 30, 2005, which is hereby incorporated by reference.

BACKGROUND

1. Field

The present embodiments relate to an electrically conductive connection in a radiation therapy system.

2. Related Art

Radiation therapy and in particular particle therapy for treating cancers is becoming increasingly important. Photon or ion therapies are examples of different particle therapies. Ion therapy utilizes protons or heavy ions. Particle therapy is generally used when the conventional X-radiation cannot adequately radiate a tumor because the tumor is seated too deep in the body or is surrounded by vulnerable organs. Particle therapy is generally performed with the aid of a rotatable beam guide, for example, a gantry.

The electrical components and consumers in a gantry require a considerable amount of current and must be triggered. Power supply, control, and data lines are supplied via cords (supply lines). The long length of the supply lines creates limitations in mobility and in the operating speed of the treatment system.

International Patent Disclosure WO 2004/026401 discloses an arrangement for performing proton therapy. As disclosed, the gantry is supported rotatably in the direction of the beam course, by an angle of between 180° and 270° about a horizontal axis. A cord supplies the electricity. The cord is coiled up on a cable drum located next to the gantry.

German Patent Disclosure DE 101 46 210 A1 discloses a computed tomography system. The computed tomography system includes a gantry supported rotatably in a housing. An X-ray source, an X-ray detector and a data detection device are disposed on the gantry. The X-ray detector is diametrically opposite the X-ray source. The electrical terminals of the X-ray source, X-ray detector, and data detection device are accomplished by way of sliprings.

Accordingly, an arrangement for an electrically conductive connection between a rotatable gantry and a stand is desired.

SUMMARY

In one embodiment, an electrically conductive connection connects a gantry, rotatable about a pivot axis, and a stand. The electrically conductive connection includes a wireless electrical contact, and at least one defined rotary positions of the gantry. The electrically conductive connection avoids burn out at the site of the electrically conductive connection in the defined rotary position are provided.

In one embodiment, the wireless or cordless electrical contact is provided by a slipring. In this embodiment, the electrical connection, for example, the electrical power supply, is made via a mechanical sliding contact via brushes or rollers, or via a contactless contact. The slipring is electrically conductive and made from any suitable material.

The wireless electrical contact supplies electrical current to components in the gantry. Alternatively or additionally, data transmission from and to the components of the gantry is possible through the wireless electrical contact.

The stand is embodied such that it is capable of transmitting electrical currents or data signals. In one embodiment, the stand extends only partway over the outer circumference of the gantry. Alternatively, the stand surrounds the gantry all the way around in the form of a ring or sleeve. In one embodiment, wireless electrical contacts are provided at a plurality of sites.

During operation of the radiation therapy system, generally one or more rotary positions of the gantry are defined, such as the 90° or 180° rotary positions (vertical and horizontal irradiation of a patient). The risk of wear in these rotary positions is especially high because these rotary positions are frequently assumed. To assure a long service life of the electrically conductive connection, according to one embodiment at least one defined rotary position of the gantry is provided. In one embodiment a means for avoiding burn-out at the site of the electrically conductive connection in the defined rotary position is provided. These may be a static or dynamic means, whose use minimizes the risk of burn-out, especially on the gantry, from a punctiform current transmission between the stand and the gantry. The means may be provided on both the side of the gantry and the side of the stand.

Reducing the risk of burn-out at the site of the electrically conductive connection creates safer operation of the gantry over a long period of time. The gantry is free to rotate having to be moved to a central position. Rotary motions of more than 360° are therefore possible. A cable drum is not required, so the structure is compact.

In one embodiment, the stand is rotatable, and the wireless electrical contact is displaceable by the rotatable stand in the circumferential direction of the gantry. In one embodiment, the stand or an electrically conductive part of the stand is slightly offset in the circumferential direction of the gantry. This slight offset suffices to avoid unwanted burning sites upon the transmission of currents of high current density. A continuous pivoting motion of the stand prevents punctiform contacts over a relatively long time.

In another embodiment, the wireless or cordless electrical contact is reinforced for the at least one defined rotary position of the gantry, which assures an electrical connection between the stand and the gantry that is secure even over long periods in the defined rotary positions. In this embodiment, the electrical contact is reinforced at the defined rotary position in such a way that it is more secure against wear. For example, a greater material thickness and/or widening the slipring in the defined, locally limited regions are provided.

In one embodiment, a plurality of contacts forms a common supply line. The common supply line supplies current to the electrical components or consumers of the gantry. The quantity of current transmitted via the individual contacts is reduced because of the distribution to a plurality of contacts. The individual contact only has a slight electrical load and has a long service life.

In another embodiment, the wireless electrical contact is disposed on the circumference of the gantry. For example, the wireless electrical contact extends annularly around the gantry in the circumferential direction. Upon a rotary motion of the gantry, different regions of the contact are loaded, and a punctiform load which could lead to a punctiform burn-out of the contact is avoided.

In one embodiment, the wireless electrical contact, or a second wireless electrical contact, is disposed on the face end of the gantry. A face-end contact is distinguished by only slight relative motion between the rotating contact element and the fixed contact element. A mechanical sliding contact only experiences a slight mechanical wear.

In one embodiment, the gantry has a component part that includes a large portion of the electrical contacts. The wireless electrical connection, or a second wireless electrical connection, is made in the immediate vicinity of this component part. The electrical contact is located in the immediate vicinity of the consumers and/or electrical components. The electrically conductive connections are made directly to the consumers, without the stand having to extend over the full length of the gantry. In an alternate embodiment, a plurality of electrical contacts are distributed over the length of the gantry and positioned in the immediate vicinity of the components to be supplied. In comparison to a design in which the gantry is electrically connected centrally via only one point, the number and length of electrical supply lines inside the gantry is reduced.

In one embodiment, the wireless electrical contact is a mechanical sliding contact. The electrical contact power in a mechanical sliding contact is, for example, simple and operationally reliable. Mechanical sliprings are understood to be both sliprings with brushes or rollers and liquid-metal arrangements. Mechanical sliding contacts, for example, brushes or rollers have a compact design and mechanical stability, long service life, and wide temperature range. Alternatively, liquid-metal arrangements are free from mechanical wear.

In another embodiment, the wireless electrical contact is contactless. For example, optical, inductive and capacitive connections have proved especially suitable.

In another embodiment, a radiation therapy system includes an electrically conductive connection between a gantry and a stand. The electrically conductive connection has a wireless electrical contact, and at least one defined rotary position of the gantry.

In another embodiment, a method for operating a gantry of a radiation therapy system includes an electrically conductive connection between the gantry and a stand. The electrically conductive connection includes a wireless electrical contact, and at least one defined rotary position of the gantry.

BRIEF DESCRIPTION OF THE DRAWINGS

FIG. 1 illustrates a gantry with a plurality of contacts contacting a supply line;

FIG. 2 illustrates a plurality of contacts at different sites of the gantry;

FIG. 3 illustrates a gantry having an inductive connection; and

FIG. 4 illustrates a gantry with a displaceable stand.

DETAILED DESCRIPTION

In one embodiment, as shown in FIG. 1, a particle therapy system 7 includes an electrically conductive connection 2 between a gantry 4, rotatable about an axis A, and a stand 6. The particle therapy system 7 provides radiation therapy for a patient with the aid of heavy ions. The electrical connection 2 is wireless. The electrical connection includes a number of electrical contacts 8 that are embodied in the manner of a slipring 10 with an associated brush 12. The sliprings 10 extend around the outer circumferential side of the gantry 4.

The electrical contacts 8 contact a supply line 14. The electrical contacts 8 are electrically connected to the rear component part 16 of the gantry 4. The rear component part 16 includes the component parts of a central system for the electrical supply to the individual electrical components of the gantry 4 (which are not shown here). The gantry 4 has a middle component part 18 and a front component part 20. Generally, a large portion of the electrical components 20 are located in the front component part and are connected via internal supply lines to the central system for electrical supply.

In one embodiment, as shown in FIG. 2, a gantry 4 is connected electrically, via a plurality of slipring contacts 8, at a plurality of sites on the circumference and face end (left side of the rear component part 16), to a stand 6. The stand 6 is embodied in two parts. The slipring contacts 8 are grouped into three supply lines 14a, 14b, 14c. The rear component part 16 of the gantry is supplied electrically via the first supply line 14a.

In one embodiment, the second supply line 14b is electrically connected to the rear component part 16 of the gantry 4. The second supply line 14b is electrically connected to the stand 6 on the face end. The reduced relative motion between the contact elements (i.e. brush 12 and slipring 10) reduces the mechanical wear of the connection elements.

In another embodiment, the third supply line 14c is disposed at the front part 20 of the gantry 4, where a large amount of the energy is needed, so that at least some of the electrical components are directly supplied with current. In this embodiment, the electrical connection is distributed over the gantry 4, for example, the electrical connection is as much as possible in the immediate vicinity of the components to be supplied.

In one embodiment, as shown in FIG. 3, a supply line 14 and a contactless contact 22 provide an electrically conductive connection to the gantry 4. In this embodiment, the wireless electrical contact 22 is provided in middle part 18 of the gantry 4 and is effected inductively via a stationary transmitter 24 and a receiver 26 that rotates with the gantry. The transmitter may simultaneously be the receiver, and the receiver can simultaneously be the transmitter. A bidirectional data transfer or power transfer is possible. The wireless contact 22 is not limited to the middle part 18, for example, the wireless contact 22 may be provided at the face end or in the front part of the gantry 4.

In one embodiment, the stand 6 is displaceable. A fixed gantry 4 with at least one encompassing slipring 10 and a displaceable stand 6 can avoid a punctiform contact transmission that can lead to burn-out. As illustrated schematically in the right-hand half of FIG. 4, the stand 6 is shown in dashed lines at a position that is displaced by approximately 60° in the circumferential direction U. Three brushes 12 are disposed in a row on the outer circumference the gantry 4. The brushes 12 slide on the slipring 10 and establish an electrically conductive connection. During operation, the stand 6 executes a pivoting motion, so the brushes 12 are displaced in the circumferential direction U of the gantry 4, without interrupting the contact 8. Preferably, the stand 6 is pivoted constantly back and forth during operation, for example, when the gantry 4 remains in the fixed rotary position. As an alternative to the pivoting motion in the direction of revolution U, the stand 6 is displaced longitudinally, parallel to the pivot axis A.

While the invention has been described above by reference to various embodiments, it should be understood that many changes and modifications can be made without departing from the scope of the invention. It is therefore intended that the foregoing detailed description be regarded as illustrative rater than limiting, and that it be understood that it is the following claims, including all equivalents, that are intended to define the spirit and scope of this invention.

The invention claimed is:

1. An electrically conductive connection that connects a gantry and a stand of a radiation therapy system, the gantry being rotatable about a pivot axis to at least one stationary position, the connection comprising: a wireless electrical contact that is displaceable in a circumferential direction of the gantry using a displacement of the stand, wherein the stand is operable to be displaced, during an operation of the radiation therapy system, to avoid burn out at a site of the wireless electrical contact at the at least one stationary position of the gantry.

2. The connection as defined by claim 1, wherein the wireless electrical contact is reinforced for the at least one stationary position of the gantry.

3. The connection as defined by claim 1, wherein a plurality of wireless electrical contacts are provided for a single supply line.

4. The connection as defined by claim 1, wherein the wireless electrical contact is disposed on the circumference of the gantry.

5. The connection as defined by claim 1, wherein the wireless electrical contact is disposed on a face end of the gantry.

6. The connection as defined by claim 1, wherein the wireless electrical contact contacts the gantry in the immediate vicinity of an electrical component part.

7. The connection as defined by claim 1, wherein the wireless electrical contact is a mechanical sliding contact.

8. The connection as defined by claim 1, wherein the wireless electrical contact is contactless.

9. The connection as defined by claim 1, wherein the wireless electrical contact is a slipring.

10. The connection as defined by claim 1, wherein the stand is operable to be rotated about a circumference of the gantry.

11. A radiation therapy system comprising:
   a gantry that is rotatable about an axis to at least one stationary position;
   a stand that is operable to be displaced during a radiation therapy operation; and
   a cordless electrical conductive contact connecting the gantry and the stand at a first contact position,
   wherein a displacement of the stand is operable to displace the cordless electrical conductive contact, during the operation of the radiation therapy system, to avoid burn out at the first contact position of the wireless electrical contact.

12. The radiation therapy system as defined by claim 11, wherein the cordless electrical contact is disposed on the circumference of the gantry.

13. The radiation therapy system as defined by claim 11 wherein a plurality of wireless electrical contacts are provided for a single supply line.

14. The radiation therapy system as defined by claim 11, wherein a displacement of the stand include a rotation of the stand about a circumference of the gantry.

15. A method for operating a gantry of a radiation therapy system, comprising:
   providing an electrically conductive connection between the gantry and a stand at a first contact position, the electrically conductive connection comprising a wireless electrical contact;
   rotating the gantry to a desired position;
   performing radiation therapy; and
   displacing the electrically conductive connection relative to the gantry, during the radiation therapy, to avoid burnout at the first contact position.

16. The method as defined by claim 15, wherein the wireless electrical contact is disposed on the circumference of the gantry.

17. The method as defined by claim 15, wherein displacing the stand and the electrically conductive connection includes rotating the stand and the electrically conductive connection about a circumference of the gantry.

* * * * *